United States Patent [19]
Kondo et al.

[11] Patent Number: 4,494,409
[45] Date of Patent: Jan. 22, 1985

[54] ENGINE VIBRATION SENSOR

[75] Inventors: Haruyoshi Kondo; Koji Tsukada; Masaharu Takeuchi, all of Aichi, Japan

[73] Assignee: Kabushiki Kaisha Toyota Chuo Kenkyusho, Aichi, Japan

[21] Appl. No.: 382,305

[22] Filed: May 26, 1982

[30] Foreign Application Priority Data

May 29, 1981 [JP] Japan ................... 56-80020
Jun. 16, 1981 [JP] Japan ................... 56-88334

[51] Int. Cl.³ ................ G01L 23/22; G01H 1/08
[52] U.S. Cl. ................ 73/651; 73/654; 73/35
[58] Field of Search ........... 73/35, 651, 654, 658; 310/329, 330, 331, 332, 25

[56] References Cited

U.S. PATENT DOCUMENTS

| | | | |
|---|---|---|---|
| 2,300,638 | 11/1942 | Wente | 310/25 |
| 3,370,187 | 2/1968 | Straube | 310/330 |
| 4,140,936 | 2/1979 | Bullock | 310/331 |
| 4,250,757 | 2/1981 | Hanson | 73/517 B |
| 4,275,586 | 6/1981 | Gast | 73/35 |
| 4,279,159 | 7/1981 | Powell et al. | 73/651 |
| 4,305,298 | 12/1981 | Greenwood | 73/651 |
| 4,348,905 | 9/1982 | Nishimura et al. | 73/654 |
| 4,374,472 | 2/1983 | Nishimura | 73/35 |
| 4,379,403 | 4/1983 | Hattori et al. | 73/35 |

Primary Examiner—James J. Gill
Attorney, Agent, or Firm—Koda & Androlia

[57] ABSTRACT

An engine vibration sensor for detecting the engine vibration as an electric signal including a vibrator set to resonate at a specific frequency of vibration of an engine to which it is attached, the vibrator being composed of at least one piezoelectric plate and having a root and a vibrator element; means for increasing the cross-sectional area of the vibrator element to make the second moment of area of the root of the vibrator relatively larger than that of the vibrator element; a base to be connected to an engine body; and a clamp for retaining the root firmly between the clamp and the base. The clamp may be provided with a projection having a flat surface for retaining the root of the vibrator. This construction prevents a change in the effective length of the vibrator element, thereby stabilizing the characteristics of the resonant frequency of the vibrator.

22 Claims, 27 Drawing Figures

ENGINE VIBRATION SENSOR

BACKGROUND OF THE INVENTION

1. Field of the Invention

This invention relates to an engine vibration sensor, more particularly to an engine vibration sensor which comprises a vibrator set to resonate at a predetermined, specific frequency of vibration of the engine to which it is attached, the vibration of the vibrator being converted into an electric signal representing the engine vibration.

2. Description of the Prior Art

Engines play an important role in ships, automobiles and many other devices and machines that contribute greatly to the quality of modern life. However, unless an engine is used under optimum operating conditions it is apt to suffer a decline in power output, abnormal vibration, abnormal wear and/or a decrease in fuel efficiency.

In order to assure that an engine is operating under optimum conditions, it is necessary to accurately monitor its actual operating state. One device known to be highly useful for this purpose is the engine vibration sensor. The usefulness of this device derives from the fact that the vibration of an engine at specific frequencies accurately reflects the operating state of the engine so that by measuring the magnitude and characteristics of the vibration at specific frequencies there can be obtained a considerable amount of data for use in optimizing the engine operating conditions. The specific frequency or frequencies selected for monitoring depend on the actual operating state of the engine. In the following, a specific example will be described in connection with the knocking vibration frequency of an engine.

Ordinarily, when ignition occurs too early in an engine, knocking and decreased power result. A decrease in power also occurs when the ignition is too late. It is therefore necessary to optimize the ignition advance so as to obtain maximum power and operating efficiency without causing the engine to knock. It is, however, no easy matter to determine the optimum value beforehand since it is dependent on the type of engine, the specific character of the engine, the number of revolutions and the intake pressure. Conventionally, the ignition advance has been set mechanically or electrically on the basis of the engine speed and the intake pressure. This method does not, however, always result in the optimum ignition advance. What has been done in actual practice, therefore, was to set the advance angle slightly smaller than the optimum value in order to prevent knocking, even though this meant that it was impossible to realize maximum power.

This expedient is no longer satisfactory since it runs counter to current demands for better engine fuel economy and fuel efficiency. The need for optimizing ignition advance is particularly strong in the case of the turbocharged engines that are being developed specifically for the purpose of reducing fuel consumption and boosting power. To meet the requirements of these engines there has been developed a knock control system for obtaining maximum efficiency wherein the ignition advance is automatically controlled using trace knocking as an index. For this system to operate effectively it is necessary to be able to measure the trace knocking of the engine quickly and accurately. Several types of engine vibration sensors have been developed and used for this purpose.

These known sensors include magnetostrictive, piezoelectric disk, piezoelectric cantilever and various other types, but none has been able to provide the required performance. For example, some are capable of precise measurement only within a limited temperature range while others can provide reliable results only at specific engine rotational speeds or under other specific measurement conditions. As a result, it has been difficult to carry out reliable engine knock control. Because of this, there has been desired a vibration sensor capable of reliably distinguishing between vibration peculiar to knocking and other miscellaneous types of vibration regardless of changes in the engine speed, temperature and other measurement conditions. Also, as most engines are of the multi-cylinder type, there has been desired a sensor capable of measuring the knocking vibration at a number of cylinders so as to make it possible to use a single sensor for optimizing the ignition advance for all cylinders of a multi-cylinder engine.

Figures 1A, 1B:
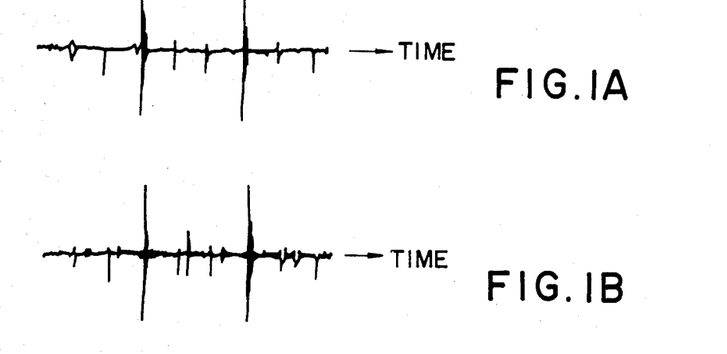
FIG. 1A is a wave form chart of an engine vibration in a normal combustion state measured by using a vibration sensor having flat frequency characteristics.
FIG. 1B is a wave form chart of an engine vibration in an abnormal combustion state measured by using a vibration sensor having flat frequency characteristics.

FIG. 1 shows engine vibration waveforms obtained by attaching a non-resonating vibrator having flat frequency characteristics to an engine and converting the engine vibration obtained through this vibrator to an electrical signal. The waveform shown in FIG. 1A is that obtained for an engine operating under a normal state of combustion without knocking while that shown in FIG. 1B is that obtained for an engine operating under an abnormal state of combustion with knocking. It will be noted from these graphs that in both cases the vibration wave periodically grows large in amplitude in synchronization with the combustion timing. In the case of FIG. 1B showing the waveform for an abnormal state of combustion, however, in addition to the periodic large amplitude waves there can be seen large amplitude vibration waves at positions somewhat shifted from the timing of the vibration peaks.

Figure 2A:
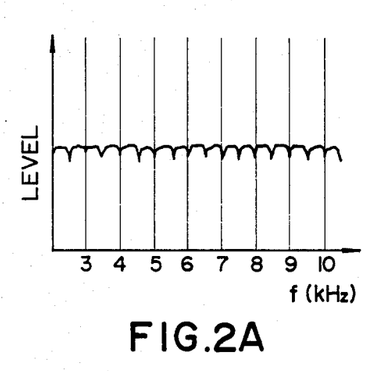
FIG. 2A is a graph showing the frequency spectrum of the vibration wave form shown in FIG. 1A.
Figure 2B:
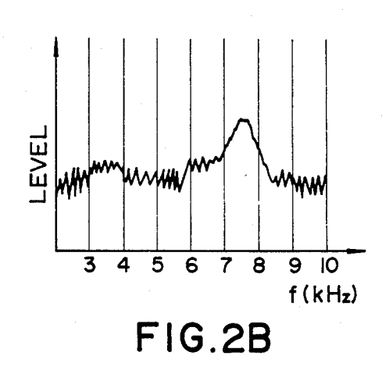
FIG. 2B is a graph showing the frequency spectrum of the vibration wave form shown in FIG. 1B.

FIG. 2 shows the frequency spectra for the waveforms shown in FIGS. 1A and 1B. FIG. 2A shows the frequency spectrum for an engine operating under a normal state of combustion without knocking and FIG. 2B shows the frequency spectrum for an engine operating under an abnormal state of combustion with knocking. As is clear from these two graphs, the frequency spectrum in the case of normal combustion with no knocking is flat while that in the case of abnormal combustion with knocking is characterized by the occurrence of peaks at a specific frequency region.

Figure 3:
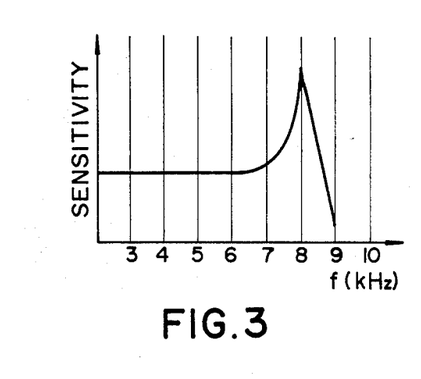
FIG. 3 is a graph showing the frequency characteristics of the vibrator of a resonating type vibration sensor.

Thus the vibration generated by knocking occurs within a frequency range extending from about 6 to 8 KHz while general vibration not related to knocking is spread over a wide range of frequencies. Because of this, by using a vibration sensor provided with a vibrator having resonant frequency characteristics which, as shown in FIG. 3, are coincident with the knocking vibration frequencies, it is possible to measure the engine's knocking vibration independently of its other general vibration.

In the case of the conventional vibrator sensors used heretofore, however, it is often difficult to make the resonant frequency of the vibrator coincide with the knocking vibration frequency and under some measurement conditions the resonant frequency of the vibration sensor will be different from the knocking vibration frequency. When the two frequencies fail to coincide, the sensor becomes incapable of distinguishing between the general vibration arising from various parts of the engine and the vibration peculiar to knocking, meaning that the measurement characteristics of the sensor will be degraded.

The causes behind this degradation in measurement characteristics can be divided into those arising from the vibration sensor and those arising from the engine.

Figure 4A:
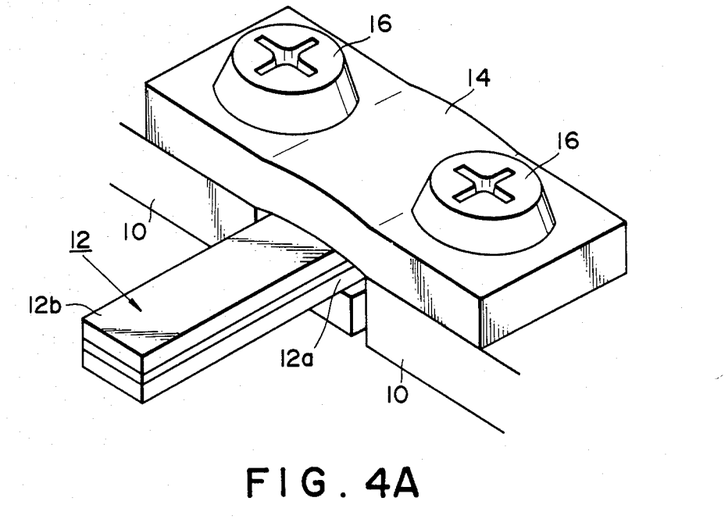
FIG. 4A is an explanatory view showing an example of the engine vibration sensor of prior art.
Figure 4B:
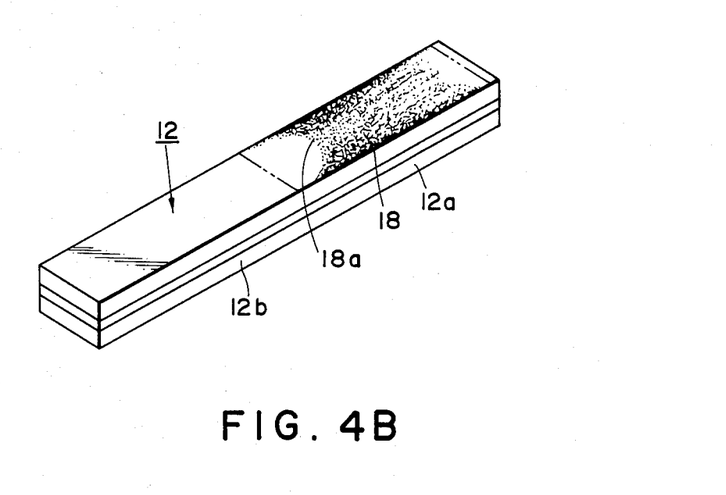
FIG. 4B is an explanatory view showing the vibrator illustrated in FIG. 4A.

The first cause is that the effective length of the vibrator element changes with the vibration. FIG. 4A is an illustration showing a conventional cantilevered vibration sensor, and FIG. 4B shows an illustration of a vibrator. In FIG. 4A, the root 12a of the vibrator 12 is clamped to the base 10 by a clamp 14 which is firmly fixed to the base 10 by screws 16. The retaining force by the clamp 14 forms such press mark 18 on the surface of the root 12a of the vibrator 12 as shown in black in FIG. 4B, and the press mark 18 is formed considerably back inside from the edge of the clamp 14 as shown in two dot chain line.

The effective length of the vibrator element 12b of the vibrator 12 is determined at the vibrator element side edge 18a of the press mark 18, and the resonant frequency of the vibrator element 12b changes inversely proportional to the square of the effective length of the vibrator element 12b. Accordingly, in order to fix the resonant frequency of the vibrator element 12b the vibrator element side edge 18a of the press mark 18 must be set definite and the effective length of the vibrator element 12b must be fixed. The vibrator element side edge 18a of the press mark 18, however, changes with the retaining force of the clamp 14, temperature and characteristic deterioration of the vibrator itself, the causes of which vary the resonant frequency characteristics of the vibrator element 12b. In addition to the above, the vibrator element side edge 18a of the press mark 18 changes with poor quality of the vibration sensor parts made in the manufacturing process, and the poor quality becomes the cause which varies the resonant frequency characteristics of the vibrator element 12b.

The second cause that can be mentioned in conjunction with the vibration sencer is the concentration of the retaining force of the clamp 14. As evident from FIG. 4B, the press mark 18 appears vaguely in the center portion and intensively on the peripheral portions of the root 12a of the vibrator 12. It is understood that the retaining force of the clamp 14 is concentrated on the peripheral sides of the root 12a of the vibrator 12. Since a piezoelectric element is attached on the surface of the vibrator element 12b for the vibrator sensor in most cases and the piezoelectric element is generally of fragile nature, there arise such drawbacks that the concentration of the retaining force causes cracks to change the resonant frequency characteristics of the vibrator element 12b.

SUMMARY OF THE INVENTION

Accordingly, it is a general object of the present invention to provide an engine vibration sensor capable of accurately measuring specific vibration of frequencies of an engine, for example the knocking frequencies thereof, separately from other general vibrations of the engine, whereby it is made possible to control the engine to operate at the optimum condition.

The engine vibration sensor according to the present invention includes a vibrator set to resonate at a predetermined, specific frequency of vibration of the engine to which it is attached, wherein the vibration of the vibrator is converted to an electric signal representing the engine vibration, said vibrator comprising a root and a vibrator element, and wherein a clamp is provided to fasten the root of the vibrator to a base so that the cross-sectional area of the vibrator element is increased to make the second moment of area of the root of the vibrator is set relatively larger than the second moment of area of the vibrator element.

DETAILED DESCRIPTION OF THE EMBODIMENTS

The present invention will hereinafter be described in further detail with reference to the accompanied drawings.

Figure 5:
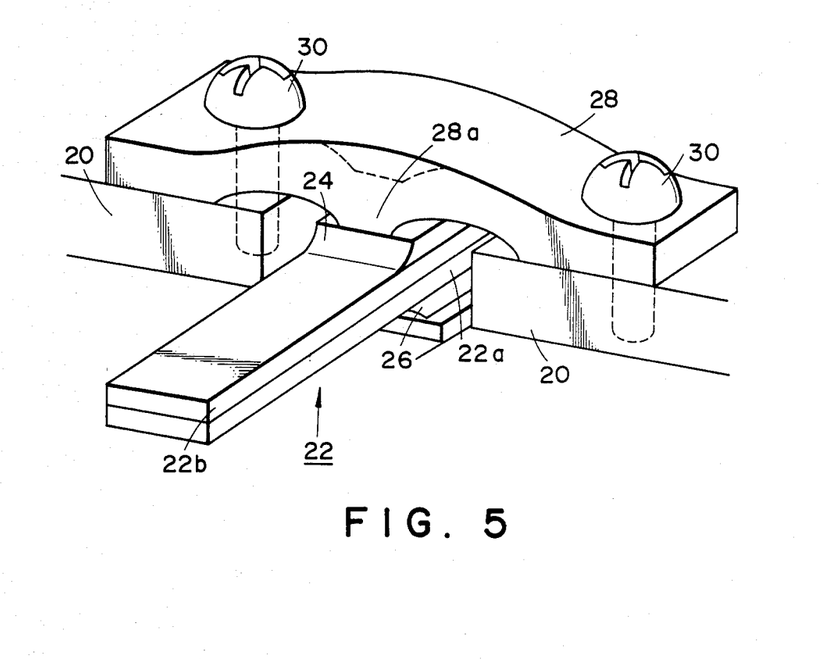
FIG. 5 is an explanatory view showing a preferred embodiment of the engine vibration sensor in accordance with the teachings of the present invention.

FIG. 5 shows a preferred embodiment of the present invention. The vibration sensor has a base 20 integrally attached to the engine body and a vibrator 22 which vibrates synchronously with the vibration of the engine in a sandwiched state between a pair of auxiliary supporters 24 and 26, being clamped by a clamp 28 which is firmly fixed to the base 20 by screws 30.

The vibrator 22 includes a root 22a and a vibrator element 22b which are composed of a pair of piezoelectric plates with an equal thickness. The root 22a of the vibrator 22 is sandwiched by a pair of the auxiliary supporters 24 and 26 so that the second moment of area of the root 22a of the vibrator 22 is set relatively larger than the second moment of area of the vibrator element 22b.

The clamp 28 for clamping the vibrator 22 onto the base 20 has a projection 28a in its center portion along the vibrator 22 in order to retain one auxiliary supporter 24, and is firmly fastened to the base 20 by screws 30.

The vibrator 22 also has a detector (not shown) for converting the mechanical vibration of the vibrator 22 into an electric signal. By setting the resonant frequency of the vibrator 22 to the knocking vibration frequency of the engine it becomes possible to electrically detect the state of knocking of the engine.

The present invention is characterized in that the second moment of area of the root 22a of the vibrator 22 is set relatively larger than the second moment of area of the vibrator element 22b.

The embodiment of the present invention is constructed as described above. The root 22a of the vibrator 22 having equal thickness is sandwiched between a pair of auxiliary supporters 24 and 26 so that the root 22a of the vibrator 22 is substantially formed thicker than the vibrator element 22b. Therefore, the second moment of area of the root 22a of the vibrator 22 is set relatively larger than the second moment of area of the vibrator element 22b. In other words, as the second moment of area is in proportion to the cube of the thickness of the element, the second moment of area of the root 22a becomes 27 times the second moment of area of the vibrator element 22b by setting the thickness of the root 22a of the vibrator 22 three times that of the vibrator element 22b. (In a beam as in this embodiment, the second moment of area (I) is given by the equation $I=(1/12)bh^3$ where b is the width and h is the thickness of the vibrator.) By this construction, as the distortion in the vibrator element 22b does not affect the root 22a of the vibrator 22, the effective length of the vibrator element 22b is not extended onto the root 22a and the decrease of the resonant frequency of the vibrator element 22b can be prevented.

Furthermore, equalization of the retaining force of the clamp by a pair of the auxiliary supporters 24 and 26 diffuses the stress concentration onto the root 22a of the vibrator 22 to prevent the vibrator element 22b from cracking even if it is made from fragile piezoelectric element, etc., and characteristics of the resonant frequency can be stabilized. The equalization of the retaining force of the clamp 28 by a pair of the auxiliary supporters 24 and 26 decreases the dependabilities on retaining force, temperature and durability at the vibrator element side edge of the press mark, and not only the stability of the characteristics of the resonant frequency but also the initial unstable period can be shortened, and further the efficiency at the manufacturing process can be increased.

Furthermore, in the present invention, the clamp 28 has the projection 28a in the center portion along with the vibrator 22 in order to retain the auxiliary supporters 24 and 26, and the stress concentration onto the peripheral portion of the root 22a as occurred in the prior art device, wherein the clamp is formed concave in its center portion to press the peripheral portion of the root 22a, can be eliminated for all over the surfaces of the auxiliary supporters 24 and 26 to be equally retained. Therefore, the dependabilities on the retaining force, temperature and the durability are decreased so low that the characteristics of the resonant frequency can be increasingly stabilized.

Figure 6:
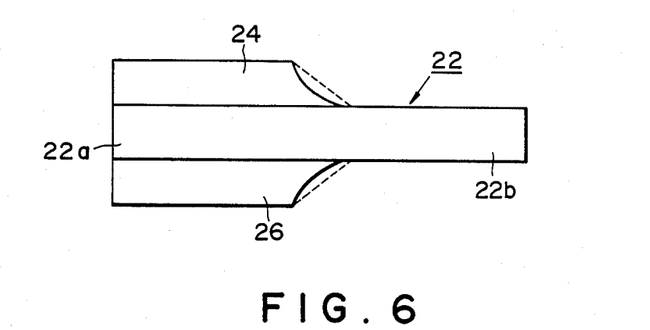
FIG. 6 is an explanatory illustration showing a modification of auxiliary supporters illustrated in FIG. 5.

It is also preferable that the vibrator element side edges of a pair of auxiliary supporters 24 and 26 be formed to gradually change in thickness as shown in FIG. 6. By forming the vibrator element side edges of the auxiliary supporters 24 and 26 in an arc or tapered shape the stress concentration onto the vibrator element side edges of the auxiliary supporters 24 and 26 can be suppressed, thereby preventing the initial unstability as well as increasing the stability of the characteristics of the resonant frequency.

Figure 7:
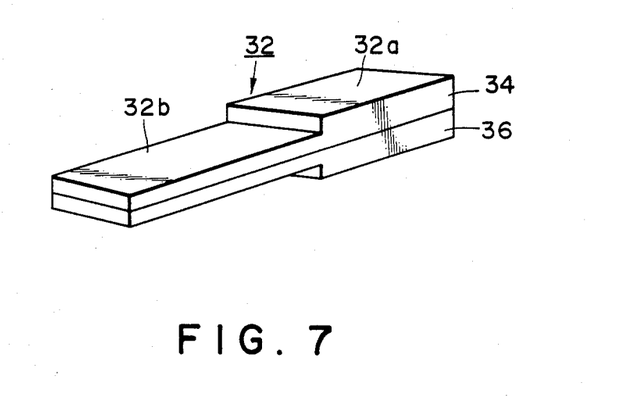
FIGS. 7 to 20 are explanatory views showing various modifications of the vibrator illustrated in FIG. 5.

FIG. 7 shows a preferred embodiment of the vibrator in the engine vibration sensor in accordance with the present invention.

The vibrator 32 is composed of a pair of piezoelectric plates 34 and 36 each having a root 32a and the vibrator element 32b integrally formed. The root 32a of the vibrator 32 is formed thicker than the vibrator element 32b. Namely, the second moment of area of the root 32a of the vibrator 32 is relatively larger than the second moment of area of the vibrator element 32b, thereby preventing the change in the effective length of the vibrator element 32b. As a result, the characteristics of the resonant frequency can be stabilized as in the embodiment described hereinbefore.

Figure 8:
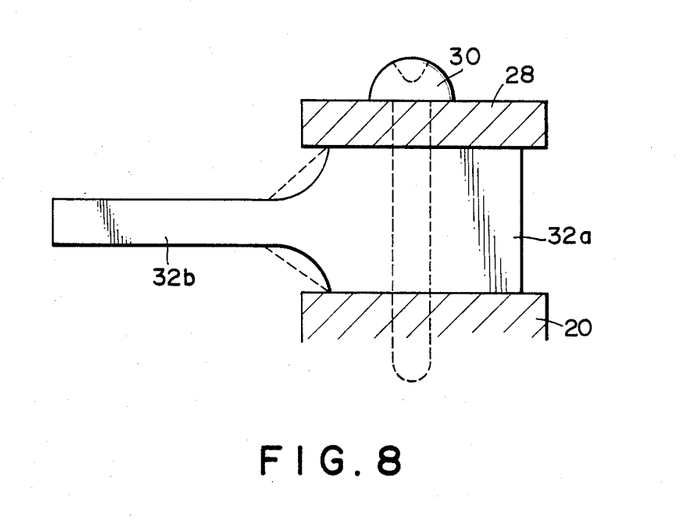

It is also preferable that the vibrator element side edges of the root 32a of the vibrator 32 is formed to gradually change in thickness as shown in FIG. 8. By forming the vibrator element side edges of the root 32a of the vibrator 32 in an arc or tapered shape, the distortion arising in the intermediate region between the root 32a and the vibrator element 32b due to the vibration can be decreased and the engine vibration sensor with high durability can be obtained.

Figure 9:
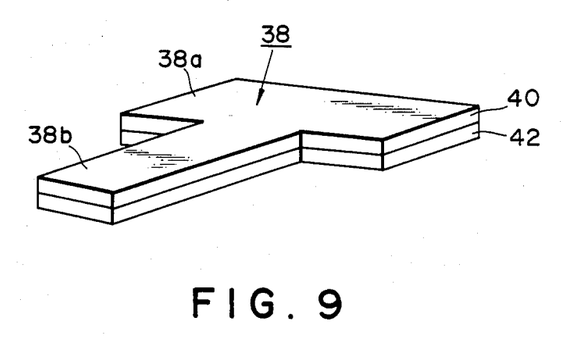

FIG. 9 shows another preferred embodiment of the vibrator of the engine vibration sensor in accordance with the present invention.

The vibrator 38 is composed of a pair of piezoelectric plates 40 and 42 adhering each other, and each having the root 38a and the vibrator element 38b integrally formed. The root 38a is formed wider than the vibrator elements 38b. Accordingly, as the second moment of area of the root 38a of the vibrator 38 is set relatively larger than the second moment of area of the vibrator element 38b, the variation in the effective length of the vibrator element 38b can be prevented and the characteristics of the resonant frequency can be stabilized as in the embodiment described heretofore.

Figure 10:
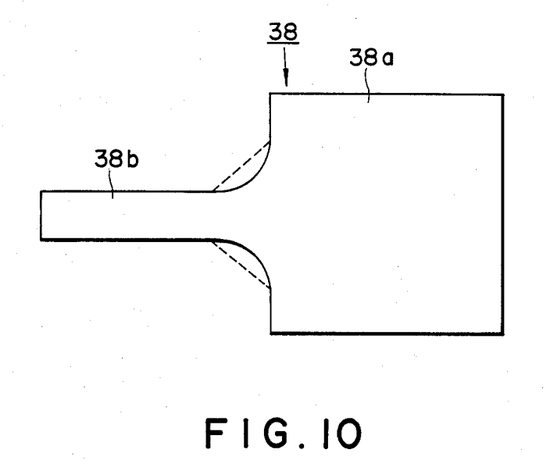

It is also preferable that the vibrator element side edges of the root 38a of the vibrator 38 are formed to gradually change in thickness as shown in FIG. 10. By forming the vibrator element side edges of the root 38a in an arc or tapered shape, the distortion arising in the intermediate region between the root 32a and the vibrator element 32b due to the vibration can be decreased and the characteristics of the resonant frequency can be stabilized.

Figure 11:
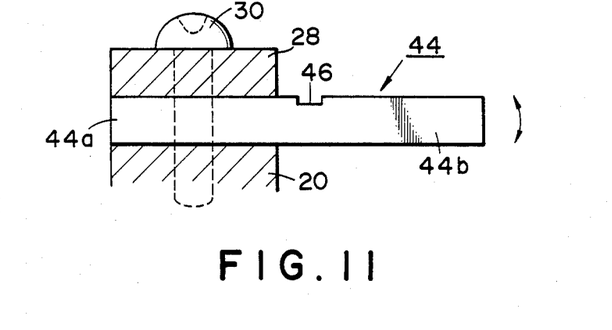
Figure 12:
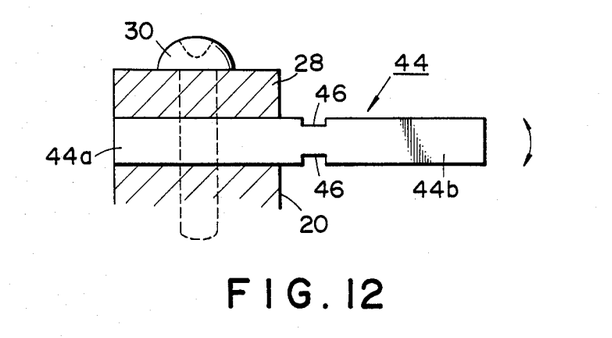
Figure 13:
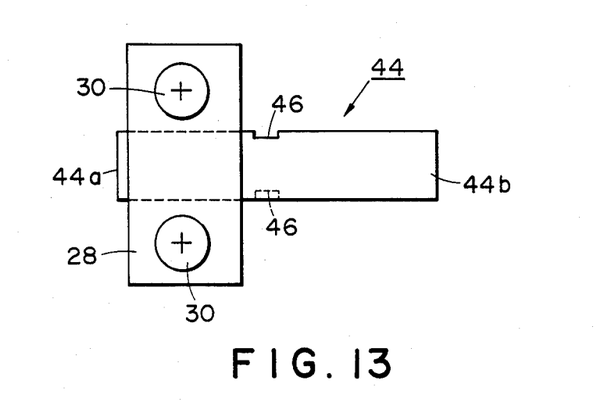

FIGS. 11 to 13 show another preferred embodiment of the vibrator of the engine vibration sensor in accordance with the present invention.

In FIG. 11, the vibrator 44 is composed of a piezoelectric plate in which, the root 44a and the vibrator element 44b are integrally formed for reducing the thickness of the vibrator element 44b and a groove 46 is provided on the upper surface at the intermediate region between the root 44a and the vibrator element 44b in order to reduced the thickness of the vibrator element. Consequently, the vibrator element 44b having the groove 46 has the relatively smaller second moment of area than the root 44a. Therefore, the second moment of area of the root 44a is set relatively larger, and the variation in the effective length of the vibrator element 44b can be prevented. The characteristics of the resonant frequency can then be stabilized in the same way with the previous embodiments described heretofore.

The grooves 46 may be provided on the upper and lower surfaces of the vibrator 44 at the intermediate region between the root 44a and the vibrator element 44b as shown in FIG. 12. The grooves 46 may also be provided on both sides or either side of the vibrator 44 at the intermediate region between the root 44a and the vibrator element 44b in order to reduce the width of the vibrator element as shown in FIG. 13. In these cases, as the second moment of area of the root 44a of the vibrator 44 can be set relatively larger than the second moment of area of the vibrator element 44b, the same effect can be obtained as in the previous embodiments described hereinabove.

Figure 14:
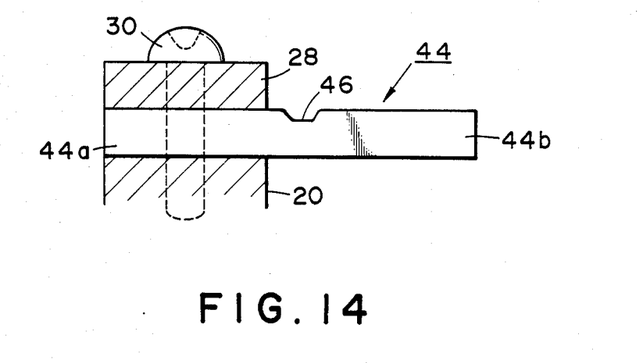
Figure 15:
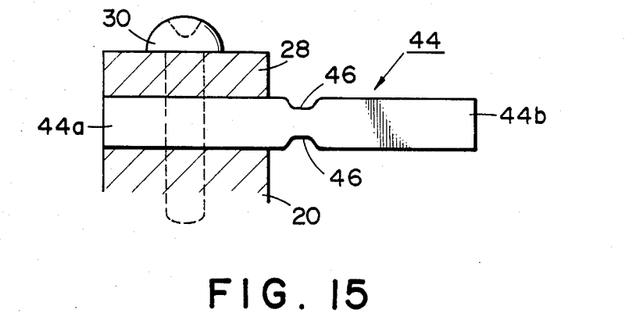
Figure 16:
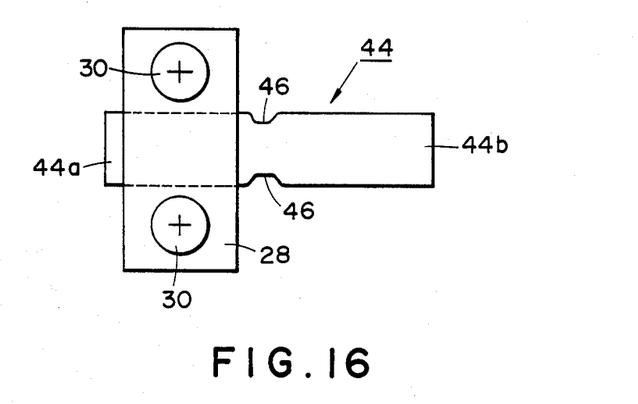

The edges of the groove 46 provided on each of the vibrators 44 shown in FIGS. 11 to 13 may be formed to gradually change in thickness as shown in FIGS. 14 to 16. By forming the edges of the groove 46 in an arc or tapered shape, the local stress concentration onto the groove 46 can be prevented and the characteristics of the resonant frequency can be stabilized.

Figure 17:
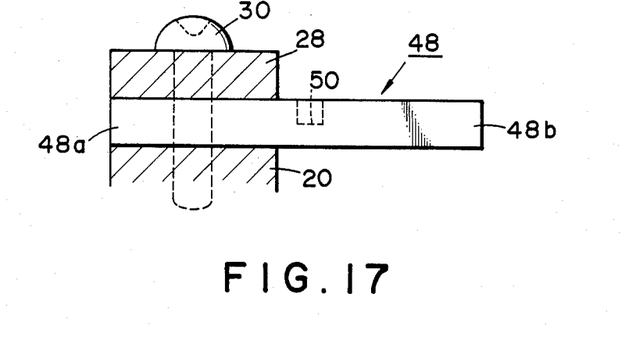

FIG. 17 shows another preferred embodiment of the vibrator of the engine vibration sensor of the present invention.

In FIG. 17, the vibrator 48 is composed of a piezoelectric plate in which the root 48a and the vibrator element 48b are integrally formed, and an opening 50 is provided on the upper surface at the intermediate region between the root 48a and the vibrator element 48b in order to reduce the width of the vibrator element 48b. Consequently, the vibrator element 48b having the opening 50 has the relatively smaller second moment of area than the root 48a. The second moment of area of the root 48a is thus set relatively larger. Therefore, the variation in the effective length of the vibrator element 48b can be prevented and the characteristics of the resonant frequency can be stabilized.

Figure 18:
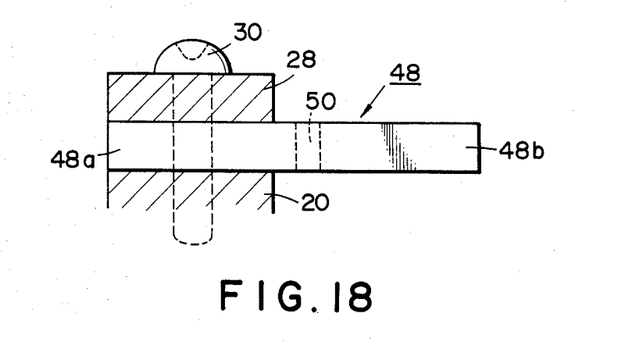
Figure 19:
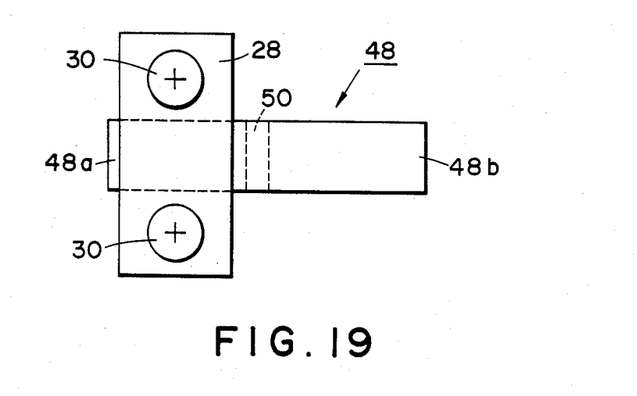

The opening 50 may be formed to penetrate through the vibrator in its thickness direction at the intermediate region between the root 48a and the vibrator element 48b as shown in FIG. 18. The opening 50 may also be formed to penetrate through the vibrator 48 in its width direction at the intermediate region between the root 48a and the vibrator element 48b as shown in FIG. 19. In these cases, the change in the effective length of the vibrator element 48b can also be prevented and the characteristics of the resonant frequency can be stabilized.

Figure 20:
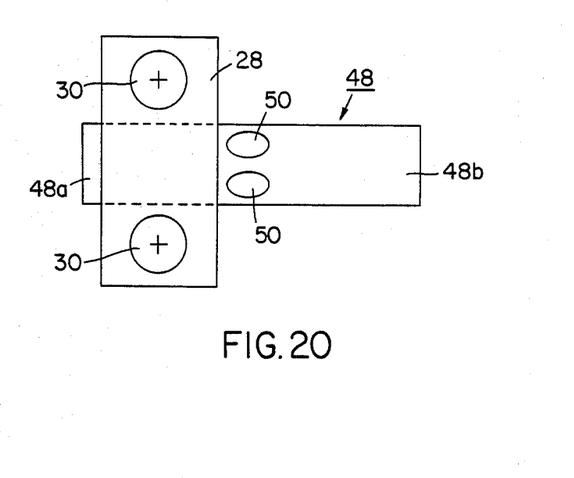

Further a plurality of openings 50 (two openings in this embodiment) may be provided as shown in FIG. 20. In this case, the same effect as in the previous embodiments can be obtained, and also a decline of stiffness against the torsion vibration of the vibrator element 48b can be suppressed. With this construction, the sensitivity to the vibration in the perpendicular direction relative to the surface of the vibrator 48 is high whereas the sensitivity to the vibration in the parallel direction is low. Therefore, the engine vibration sensor with excellent selectivity with regard to the vibrating direction can be obtained.

Although the embodiments heretofore described are directed to the cantilever type engine vibration sensor, the present invention can be applied to various types of the engine vibration sensor such as a beam type and a disc (plate) type.

Figure 21:
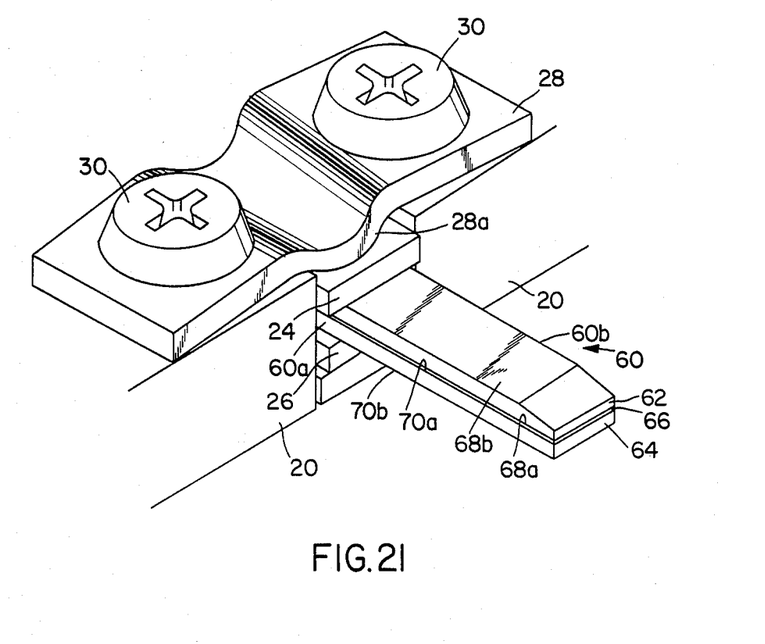
FIG. 21 is an explanatory view showing another embodiment of the vibrator sensor of the present invention.

FIG. 21 shows another embodiment of the engine vibration sensor of the present invention.

The vibrator 60 includes piezoelectric plates 62 and 64 reinforced by a conductive plate 66. On both vibrator element sides of the respective piezoelectric plates 62 and 64 are attached electrode layers 68a, 68b and 70a, 70b, and both of the piezoelectric plates 62 and 64 are fixed to both sides of the conductive plate 66 by an adhesive agent. The mechanical vibration of the vibrator 60 is converted into an electric signal. By setting the resonant frequency of the vibrator 60 to the knocking vibration frequency of the engine it is possible to electrically detect the state of knocking of the engine.

In this embodiment, in order to firmly fix the piezoelectric plates 62 and 64 to the conductive reinforcing plate 66 as well as to secure the stable conductivity between the conductive reinforcing plate 66 and the electrode layers 68a and 70a, concave and convex portions are formed on both or either of the conductive reinforcing plate 66 and/or the electrode layers 68a and 70a facing to the plate 66 so that the convex surface can cut into the facing electrode layers 68a and 70b or the conductive reinforcing plate 66 to render them stably conductive and to allow them to firmly adhere to each other by an adhesive agent filled in the concave surface.

Figure 22:
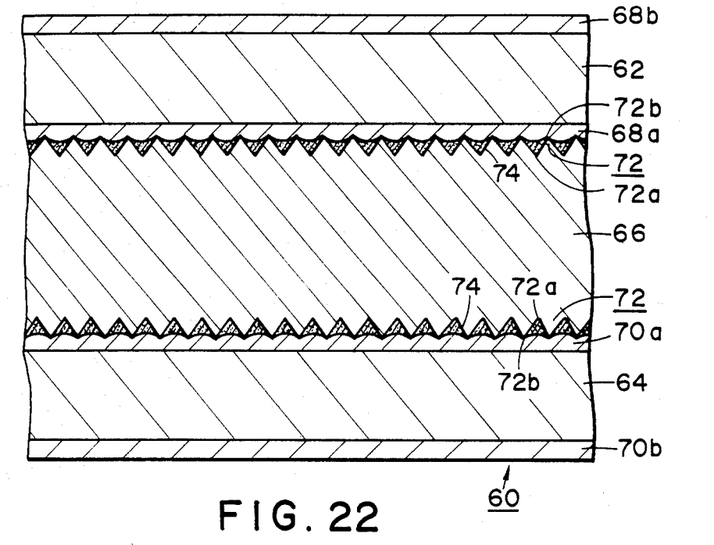
FIGS. 22 to 24 are grossly enlarged sectional views showing preferred embodiments of the vibrator of the engine vibration sensor of the present invention.

FIG. 22 is an enlarged sectional view of the portions described above. On the conductive reinforcing plate 66 are provided concave and convex portions 72, and an adhesive agent is filled in the concave portion 72a to a depth of 1/1.5 to ½ times greater than the thickness of the convex portion 72b. The above mentioned concave and convex portions 72 are formed in the dotted or creased state on the surfaces of the conductive reinforcing plate 66. In latter case it is preferable that the creases be directed longitudinally of the vibrator 60 in view of the reinforcing effect of the conductive reinforcing plate 66. In the case of forming the creases at right angles to the longitudinal direction of the vibrator 66 it is preferable that the creases are formed only in the root 60a area.

When the surfaces of the conductive reinforcing plate 66 are formed in the creased state attention should be paid to the force, and time for pressing the vibrator 60 since bubbles and surplus of the adhesive agent 74 are apt to remain at the respective convex portions 72b and the adhesive agent 74 gets thick.

Figure 23:
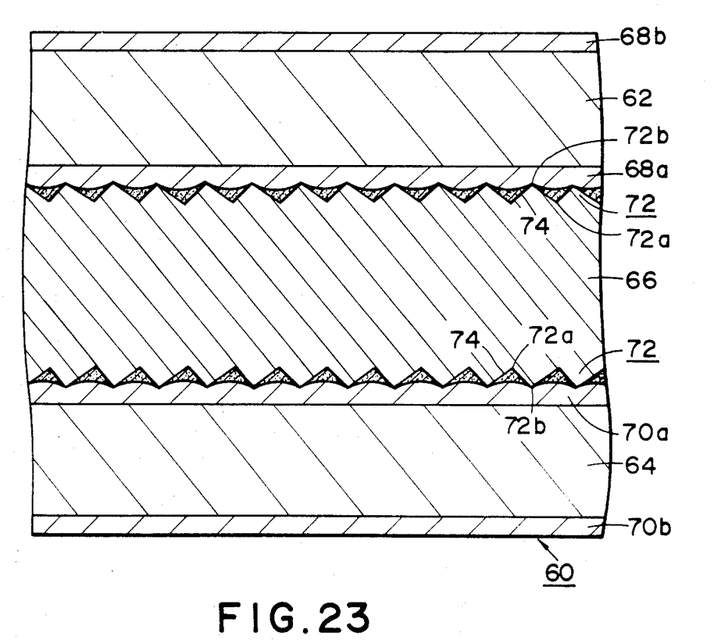
Figure 24:
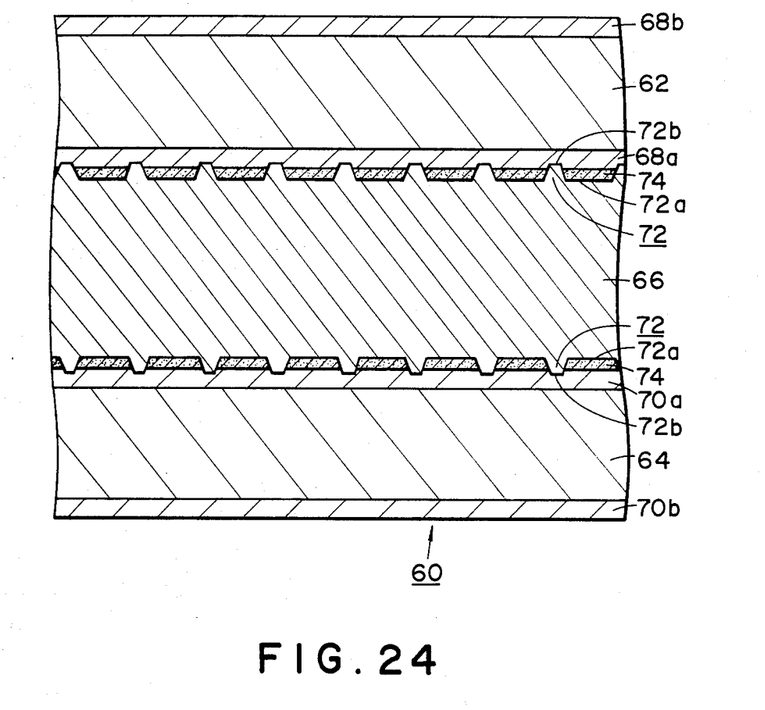

The concave and convex portions 72 of the conductive reinforcing plate 66 can be formed by press working, by means of a roller with concave and convex dies, or by means of print-etching, photo-etching, etc. The concave and convex portions 72 may be formed in the form of peaks as shown in FIG. 22 in a wave shape as shown in FIG. 23 or in a trapezoid shape as shown in FIG. 24

The piezoelectric plates 62 and 64 are pressed to the surfaces of the conductive reinforcing plate 66 so that the convex portion 72b can cut into the electrode layers 68a and 70a, which adhere to the conductive reinforcing plate 66 by the adhesive agent 74 filled in the concave portion 72a.

The construction of this embodiment is as described above, and since the convex portion 72b on the conductive reinforcing plate 66 cuts into its facing electrode layers 68a and 70a, the stable conductive conditions can be maintained.

A large force is required for breaking the adhesive agent 74 once allowed to leak from the concave portion 72a to the convex portion 72b. According to this embodiment, however, the convex portion 72b can serve to break the adhesive agent 74 on the convex portion 72b, if any, to cut into its facing electrode layers 68a and 70a since the pressing force to the vibrator 60 is concentrated on the convex portion 72b. Accordingly, the stable conductive conditions between the conductive reinforcing plate 66 and the electrode layers 68a and 70a can be obtained.

In this embodiment, the piezoelectric plates 62 and 64 can firmly adhere to the conductive reinforcing plate 66 as the large adhesive area can be secured between the conductive reinforcing plate 66 and the electrode layers 68a and 70a. Moreover, the adhering force to the piezoelectric plates 62 and 64 can be further strengthened by the convex portion 72b cutting into the piezoelectric plates 62 and 64. Unlike in conventional vibration sensor in which the special conductive adhesive agent is required to secure the optimum conductive conditions, the present embodiment can use the adhesive agent with a strong adhesive force so that, while the stable conductive conditions are secured, the piezoelectric plates 62 and 64 are allowed to firmly adhere to the conductive reinforcing plate 66. Furthermore, since the concave and convex portions 72 are formed equal in size and in density, the adhesive force and the conductivity obtained are uniform.

Although the concave and convex portions 72 are provided on the conductive reinforcing plate 66 in the embodiment, they may be provided on the electrode layers 68a and 70a or on both of the conductive reinforcing plate 66 and the electrode layers 68a and 70a.

The concave and convex portions 72 can be formed on the electrode layers 68a and 70a by pressing by use of dies with projections during desiccation after printing the electrode layers 68a and 70a, by masking in printing the electrodes or by print-etching or photo-etching.

The above embodiment is directed to adhering between the conductive reinforcing plate 66 and the electrode layers 68a and 70a, but it may be applied to adhering between the auxiliary supporters 24 and 26 and the electrode layers 68b and 70b shown in FIG. 21.

As described heretofore, according to the present invention, by relatively increasing the cross-sectional area of the vibrator element to make the second moment of area of the root of the vibrator to be relatively larger than the second moment of the area of the vibrator element, the characteristics of the resonant frequency, etc. are stabilized and the resonant frequency of the vibrator can be coincided with a specific frequency of the engine vibration, for example, the knocking vibration frequency. As a result, the present invention can offer the engine vibration sensor capable of detecting the specific vibration of the engine distinct from the other general vibration of the engine and thus operating the engine under the optimum conditions.

Furthermore, the concave and convex portions may be provided on both or either of the conductive reinforcing plate and/or its facing electrode layers to allow the convex portion to cut into the opposed electrode layers or the conductive reinforcing plate, thereby rendering them directly conductive and also allowing them to firmly adhere to each other by the adhesive agent filled in the concave portion and the stable conductivity can be secured between the conductive reinforcing plate and the electrode layers, but also the piezoelectric plates can firmly be adhered to the conductive reinforcing plate. Accordingly, by stabilizing the characteristics of the resonant frequency of the vibrator the resonant frequency of the vibrator can be coincided with the specific frequency of vibration, for example, to the knocking vibration frequency, and the present invention can offer the engine vibration sensor making it possible to detect and measure the specific vibration of the engine distinct from the other general vibration of the engine and to control the engine being operated at optimum conditions.

What is claimed is:

1. An engine vibration sensor comprising:
   a vibrator for resonating at a specific frequency of vibration of an engine to which it is attached, said vibrator being composed of a pair of piezoelectric plates attached to each other, each of said piezoelectric plates having a constant thickness and having a root and a vibrator element;
   means for relatively increasing the cross-sectional area of said root to make the second moment of area of said root larger than that of said vibrator element, said means for increasing the cross-sectional area being a pair of auxiliary supporters provided on upper and lower surfaces of said vibrator at said root thereof, for increasing the thickness of said root to make the second moment of area of said root larger than that of said vibrator element to thereby equalize the stress on said upper auxiliary support and prevent said vibrator from being damaged;
   a base to be connected to an engine body; and
   a clamp for retaining said root firmly between said clamp and said base, said clamp having a projection in the center portion thereof along said vibrator for retaining said root of said vibrator to thereby prevent said vibrator from being damaged to due stress concentration;
   thereby preventing a change in the effective length of said vibrator element and stabilizing the characteristics of the resonant frequency of said vibrator.

2. An engine vibration sensor according to claim 1, wherein edge portions of said auxiliary supporters on a vibrator element side gradually change in thickness.

3. An engine vibration sensor according to claim 2, wherein said edge portions of said auxiliary supporters linearly gradually change in thickness.

4. An engine vibration sensor according to claim 2, wherein said edge portions of said auxiliary supporters gradually change in thickness in a curved manner.

5. An engine vibration sensor according to claim 1, wherein said projection has a flat surface for engaging said upper auxiliary supporter, said projection being smaller in width than said upper auxiliary supporter to thereby prevent corner portions of said vibrator from being cracked.

6. An engine vibration sensor comprising:
   a vibrator for resonating at a specific frequency of vibration of an engine to which it is attached, said vibrator being composed of a pair of piezoelectric plates and a conductive reinforcing plate interposed between said piezoelectric plate, each of said piezoelectric plates having electrode layers attached on upper and lower surfaces thereof and said piezoelectric electric plates being fitted to said conductive reinforcing plate through said electrode layers;
   concave and convex portions provided on at least one of said conductive reinforcing plates and said electrode layers facing said conductive reinforcing plate so that said convex surface cuts into said facing elctrode layers and/or said conductive reinforcing plate to render said conductive reinforcing plate and said electrode layers stably conductive through said convex surface and to allow the same to firmly adhere to each other by an adhesive agent filled in said concave surface;

means for relatively increasing the front sectional area of said root to make the second moment of area of said root relatively larger than that of said vibrator element;

a base to be connected to an engine body; and a clamp for retaining said root firmly between said clamp and said base;

thereby preventing a change in the effective length of said vibrator element and stabilizing the characteristics of the resonant frequency of said vibrator.

7. An engine vibration sensor according to claim 6, wherein:

said means for increasing are a pair of auxiliary supporters provided on upper and lower surfaces of said vibrator at said root thereof, for increasing the thickness of said root to make the second moment of area of said root larger than that of said vibrator element; and said clamp has a projection with a flat surface for retaining said root of said vibrator with an equalized stress.

8. An engine vibration sensor according to claim 6, wherein said concave and covex portions are formed in the form of creases.

9. An engine vibration sensor according to claim 6, wherein said concave and convex portions are formed in the form of dots.

10. An engine vibration sensor according to claim 6, wherein said concave and convex portions are formed in the form of peaks.

11. An engine vibration sensor according to claim 6, wherein said concave and convex portions are formed in a waveshape.

12. An engine vibration sensor according to claim 6, wherein said concave and convex portions are formed in a trapezoidal shape.

13. An engine vibration sensor comprising:

a vibrator for resonating at a specific frequency of vibration of an engine to which it is attached, said vibrator being compared of a pair of piezoelectric plates attached to each other, each of said piezoelectric plates having a constant thickness and having a root and vibrator element;

means for relatively increasing the cross-sectional area of said root to make the second moment of area of said root relatively larger than said vibrator element, said means for increasing being a pair of auxiliary supporters provided on upper and lower surfaces of said vibrator and said root thereof, for increasing the thickness of said root to make the second moment of area of said root larger than that of said vibrator element and edge portions of said auxiliary supporters on the vibrator element side gradually change in thickness;

a base to be connected to an engine body; and a clamp for retaining said root firmly between said clamp and said base;

thereby preventing a change in the effective length of said vibrator element and stabilizing the characteristics of said resonant frequency of said vibrator.

14. An engine vibration sensor comprising:

a vibrator for resonating at a specific frequency of vibration of an engine to which it is attached, said vibrator being composed of a pair of piezoelectric plates attached to each other, each of said piezoelectric plates having a root and a vibrator element, and said root thereof being larger in thickness for making the second moment of area of said root relatively larger than that of said vibrator element;

a base to be connected to an engine body; and a clamp for retaining said root firmly between said clamp and said base, said clamp having a projection in the center portion thereof along said vibrator for retaining said root of said vibrator to thereby prevent said vibrator from being damaged due to stress concentration;

thereby preventing a change in the effective length of said vibrator element and stabilizing the characteristics of the resonant frequency of said vibrator.

15. An engine vibration sensor comprising:

a vibrator for resonating at a specific frequency of an engine to which it is attached, said vibrator being composed of at least one piezoelectric plate and having a root and a vibrator element;

means for relatively increasing the cross-sectional area of said root to make the second moment of area of said root relatively larger than that of said vibrator element, said means for increasing comprising a groove provided on at least one of upper and lower surfaces of said vibrator element near the boundary between said root and said vibrator element to thereby reduce the thickness of said vibrator element to make the second moment of area of said root of said vibrator relatively larger than that of said vibrator element;

a base to be connected to an engine body; and a clamp for retaining said root firmly between said clamp and said base;

thereby preventing a change in the effective length of said vibrator element and stabilizing the characteristics of said resonant frequency of said vibrator.

16. An engine vibration sensor according to claim 15, wherein edges of said groove gradually change in thickness.

17. An engine vibration sensor comprising:

a vibrator for resonating at a specific frequency of vibration of an engine to which it is attached, said vibrator being composed of at least one piezoelectric plate and having a root and a vibrator element;

means for relatively increasing the cross-sectional area of said root to make the second movement of area of said root relatively larger than that of said vibrator element, said means for increasing comprising a groove provided on at least one of the side surfaces of said vibrator element near the boundary beteen said root and said vibrator element to thereby reduce the width of said vibrator element to make the second moment of area of said root of said vibrator relatively larger than that of said vibrator element;

a base to be connected to an engine body; and a clamp for retaining said root firmly between said clamp and said base;

thereby preventing a change in the effective length of said vibrator element and stabilizing the characteristics of said resonant frequency of said vibrator.

18. An engine vibration sensor according to claim 17, wherein edges of said groove gradually change in width.

19. An engine vibration sensor comprising:

a vibrator for resonating at a specific frequency of vibration of an engine to which it is attached, said vibrator being composed of at least one piezoelectric plate and having a root and a vibrator element;

means for relatively increasing the cross-sectional area of said root to make the second moment of area of said root relatively larger than that of said vibrator element, said means for increasing comprising at least one opening provided in said vibrator element near the boundary between said root and said vibrator element for reducing the cross-sectional area of said vibrator element to make the second moment of area of said root relatively larger than that of said vibrator element;

a base to be connected to an engine body; and a clamp for retaining said root firmly between said clamp and said base; thereby preventing a change in the effective length of said vibrator element and stabilizing the characteristics of the resonant frequency of said vibrator.

20. An engine vibration sensor according to claim 19, wherein said opening is provided in said vibrator element in the thickness direction thereof to thereby reduce the width of the vibrator element.

21. An engine vibration sensor according to claim 19, wherein said opening penetrates through said vibrator element in the thickness direction thereof to thereby reduce the width of said vibrator element.

22. An engine vibration sensor according to claim 19, wherein said opening penetrates through said vibrator element in the width direction to thereby reduce the thickness of said vibrator element.

* * * * *